(12) United States Patent
Bower et al.

(10) Patent No.: US 11,234,605 B2
(45) Date of Patent: Feb. 1, 2022

(54) APPARATUS FOR BIOMETRIC MEASUREMENT

(71) Applicant: Nokia Technologies Oy, Espoo (FI)

(72) Inventors: Christopher Bower, Cambridge (GB); Surama Malik, Cambridge (GB)

(73) Assignee: Nokia Technologies Oy, Espoo (FI)

( * ) Notice: Subject to any disclaimer, the term of this patent is extended or adjusted under 35 U.S.C. 154(b) by 247 days.

(21) Appl. No.: 15/537,373

(22) PCT Filed: Dec. 7, 2015

(86) PCT No.: PCT/FI2015/050855
§ 371 (c)(1),
(2) Date: Jun. 16, 2017

(87) PCT Pub. No.: WO2016/097472
PCT Pub. Date: Jun. 23, 2016

(65) Prior Publication Data
US 2017/0354335 A1 Dec. 14, 2017

(30) Foreign Application Priority Data
Dec. 19, 2014 (EP) .................................... 14199095

(51) Int. Cl.
*A61B 5/024* (2006.01)
*A61B 5/00* (2006.01)
*A61B 5/1455* (2006.01)

(52) U.S. Cl.
CPC ...... *A61B 5/02427* (2013.01); *A61B 5/14552* (2013.01); *A61B 5/681* (2013.01);
(Continued)

(58) Field of Classification Search
CPC .............. A61B 5/02427; A61B 5/6898; A61B 5/14552; A61B 5/0015; A61B 2562/12;
(Continued)

(56) References Cited

U.S. PATENT DOCUMENTS 6,533,729 B1 * 3/2003 Khair ...................... A61B 5/021
600/480
6,745,061 B1 * 6/2004 Hicks ................. A61B 5/14552
600/323
(Continued)

FOREIGN PATENT DOCUMENTS

JP 2007105316 A 4/2007
JP 2013000157 A 1/2013
(Continued)

OTHER PUBLICATIONS

Pasolini, Antonio. Stretchy, health monitoring skin patch uses off-the-shelf components [online]. New Atlas, Apr. 10, 2014 [retrieved on Jul. 20, 2018], pp. 1-16. Retrieved from the Internet: [URL: https://newatlas.com/stick-on-skin-patch-health-monitoring/31507/ ]. (Year: 2014).*

(Continued)

*Primary Examiner* — Angela M Hoffa
*Assistant Examiner* — Younhee Choi
(74) *Attorney, Agent, or Firm* — Harrington & Smith (57) ABSTRACT

An apparatus comprising at least one light source, at least one photodetector, a first layer of optical material configured to embed the at least one light source, and a second layer of optical material configured to embed the at least one photodetector. The first and second layer of optical material are configured to guide light from the at least one light source and to prevent the light from the at least one light source directly reaching the at least on photodetector, and the second layer of optical material is configured to guide light towards the at least one photodetector.

10 Claims, 4 Drawing Sheets

(52) U.S. Cl.
CPC .......... *A61B 5/6802* (2013.01); *A61B 5/6833* (2013.01); *A61B 5/6898* (2013.01); *A61B 5/0015* (2013.01); *A61B 5/6832* (2013.01); *A61B 2562/0233* (2013.01); *A61B 2562/12* (2013.01)

(58) Field of Classification Search
CPC .......... A61B 2562/0233; A61B 5/6832; A61B 5/6833; A61B 5/688; A61B 5/6801; A61B 5/6802; A61B 5/6813; A61B 5/683; A61B 5/6879; A61B 5/681; A61B 5/6824
USPC ...................................................... 600/479
See application file for complete search history.

(56) References Cited

U.S. PATENT DOCUMENTS

| | | | | |
|---|---|---|---|---|
| 2004/0252867 | A1* | 12/2004 | Lan | G06K 9/0004 382/124 |
| 2009/0112071 | A1 | 4/2009 | LeBoeuf et al. | |
| 2009/0156912 | A1* | 6/2009 | Kuhn | A61B 5/0086 600/310 |
| 2009/0171177 | A1* | 7/2009 | Hannula | A61B 5/14552 600/344 |
| 2011/0004106 | A1* | 1/2011 | Iwamiya | A61B 5/02427 600/476 |
| 2011/0245637 | A1 | 10/2011 | McKenna | |
| 2013/0060098 | A1 | 3/2013 | Thomsen et al. | |
| 2013/0116520 | A1* | 5/2013 | Roham | A61B 5/6833 600/324 |
| 2014/0107493 | A1 | 4/2014 | Yuen et al. | |

FOREIGN PATENT DOCUMENTS

| | | |
|---|---|---|
| WO | 2012/103273 A2 | 8/2012 |
| WO | 2014/060641 A1 | 4/2014 |
| WO | 2014/060642 A1 | 4/2014 |
| WO | 2014/092932 A1 | 6/2014 |

OTHER PUBLICATIONS

Haahr, R. G., et al. An Electronic Patch for Wearable Health Monitoring by Reflectance Pulse Oximetry [online]. IEEE Transactions on Biomedical Circuits and Systems, 2012 [retrieved on Mar. 24, 2021]. Retrieved from the Internet: <URL: https://ieeexplore.ieee.org/document/6026927> <DOI: 10.1109/TBCAS.2011.2164247>.*

International Search Report and Written Opinion received for corresponding Patent Cooperation Treaty Application No. PCT/FI2015/050855 dated Feb. 16, 2016, 13 pages.

Cui et al., "In Vivo Reflectance of Blood and Tissue as a Function of Light Wavelength", IEEE Transactions on Biomedical Engineering, vol. 37, No. 6, Jun. 1990, pp. 632-639.

"Stretchy, Health Monitoring Skin Patch Uses Off-the-shelf Components", New Atlas, Retrieved on Jul. 20, 2018, Webpage available at: https://newatlas.com/stick-on-skin-patch-health-monitoring/31507/.

Extended European Search Report received for corresponding European Patent No. 14199095.2, dated Jun. 18, 2015, 8 pages.

Office action received for corresponding European Patent No. 14199095.2, dated Sep. 21, 2017, 8 pages.

Office action received for corresponding Japanese Patent Application No. 2017-531825, dated Jun. 6, 2018, 3 pages of office action and 3 pages of translation available.

* cited by examiner

Fig. 6

APPARATUS FOR BIOMETRIC MEASUREMENT

RELATED APPLICATION

This application was originally filed as Patent Cooperation Treaty Application No. PCT/FI2015/050855 filed Dec. 7, 2015 which claims priority benefit to EP Patent Application No. 14199095.2, filed Dec. 19, 2014.

TECHNICAL FIELD

The present application generally relates to biometric measurement. In particular, but not exclusively, the present application relates to a wearable apparatus for biometric measurement. In particular, but not exclusively, the present application relates to a skin attached apparatus for biometric measurement.

BACKGROUND

This section illustrates useful background information without admission of any technique described herein representative of the state of the art.

Wearable devices for biometric measurements are increasingly sought after and produced. Currently many devices for measuring e.g. heart rate and further biometrics are uncomfortable and bulky, i.e. not suitable or convenient to be worn for prolonged time periods.

Existing devices using optical measurement methods, such as optical photoplethysmography (PPG), are worn in contact with the skin, for example on the wrist, which is more convenient for long term use. These devices rely on illuminating the body tissue with for example IR, red, or green light emitting diodes (LEDs) and detecting the reflected light signal.

In order to attain a sufficient signal, the illumination needs to be very bright, which causes increased power consumption, and the devices need to be worn uncomfortably tightly on the skin in order to avoid artifacts due to relative movement of the skin and the measurement components.

Devices attached to the skin, akin to plasters or band aids, are known for optical biometric measurement. Such devices need to be small in size and accordingly the power source thereof is limited in size as well causing short usage times.

The present invention aims to mitigate the problems of optical biometric measurement.

SUMMARY

Various aspects of examples of the invention are set out in the claims.

According to a first example aspect of the present invention, there is provided an apparatus, comprising:
at least one light source;
at least one photodetector;
a first layer of optical material configured to embed the at least one light source; and
a second layer of optical material configured to embed the at least one photodetector; wherein
the first and second layer of optical material are configured to guide light from the at least one light source and to prevent the light from the at least one light source directly reaching the at least on photodetector; and wherein
the second layer of optical material is configured to guide light towards the at least one photodetector.

The apparatus may further comprise a substrate on which the at least one light source and the at least one photodetector are mounted.

The substrate may be flexible and/or stretchable.

The at least one photodetector may be mounted on a distance from the surface of the substrate.

The at least one light source may comprise a light emitting diode, LED.

The at least one light source may comprise an ambient light source.

The apparatus may further comprise a reflective layer and an optical element configured to function as a waveguide.

The first and/or second layer of optical material may comprise reflective or absorbing material.

The apparatus may further comprise a skin safe adhesive layer configured to embed the elements of the apparatus and configured for attaching the apparatus to the skin of a user.

The apparatus may further comprise a circuit element comprising a low power amplifier circuit.

The low power amplifier circuit may be mounted on a separate circuit element.

According to a second example aspect of the present invention, there is provided a system, comprising
the apparatus of the first example aspect; and
a power and memory element connected to the apparatus.

The power and memory element may be comprised in an independent apparatus.

The independent apparatus may comprise a personal electronic device such as a wristwatch, a smart watch, an activity bracelet, a mobile phone, a smartphone, a tablet, a computer or a television.

According to a third example aspect of the present invention, there is provided a method of manufacturing an apparatus according to the first aspect of the invention, comprising
mounting at least one light source on a substrate;
applying a first layer of optical material to embed the at least one light source;
mounting at least one photodetector on a substrate; and
applying a second layer of optical material to embed the at least one photodetector.

The method may further comprise applying a layer of skin safe adhesive.

The at least one light source may be mounted on a first substrate and the at least one photodetector may be applied on a second substrate and mounted on top of the first substrate.

Any memory medium hereinbefore or hereinafter may comprise a digital data storage such as a data disc or diskette, optical storage, magnetic storage, holographic storage, opto-magnetic storage, phase-change memory, resistive random access memory, magnetic random access memory, solid-electrolyte memory, ferroelectric random access memory, organic memory or polymer memory. The memory medium may be formed into a device without other substantial functions than storing memory or it may be formed as part of a device with other functions, including but not limited to a memory of a computer, a chip set, and a sub assembly of an electronic device. In the context of this document, a "memory medium" may be any non-transitory media or means that can contain, store, communicate, propagate or transport the instructions for use by or in connection with an instruction execution system, apparatus, or device, such as a computer.

Different non-binding example aspects and embodiments of the present invention have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE DRAWINGS

An example embodiment of the present invention and its potential advantages are understood by referring to FIGS. 1 through 5 of the drawings. In this document, like reference signs denote like parts or steps.

Figure 1:
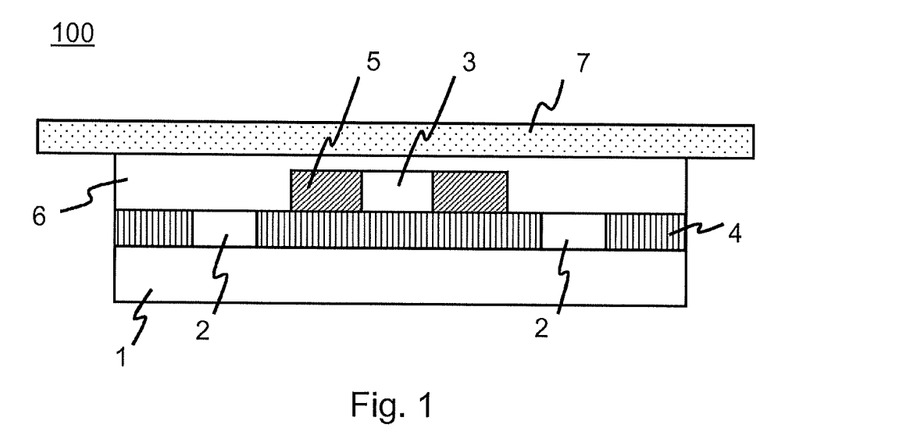
FIG. 1 shows a schematic side view of an apparatus according to an example embodiment of the invention.

FIG. 1 shows a schematic side view of an apparatus according to an example embodiment of the invention. FIG. 1 shows an apparatus 100 for optical biometric measurement according to an example embodiment. The apparatus 100 comprises a flexible and/or stretchable substrate 1. The substrate 1 has mounted thereon at least one light source 2, such as a light emitting diode (LED) or organic light emitting diode (OLED), configured to emit light towards and into the skin 7 and the blood perfused tissue of the person using the apparatus. In an example embodiment, the light source 2 is configured to emit green light.

The substrate 1 further has mounted thereon at least one photodetector 3. The at least one photodetector 3 is configured to detect the light reflected from the skin 7 and the blood perfused tissue of the person using the apparatus. In an example embodiment, the at least one photodetector 3 is mounted on a distance from the surface of the substrate 1 in order to reduce the possibility of light from the at least one light source 2 from directly reaching the at least one photodetector 3. In a further example embodiment, the at least one photodetector 3 is mounted on a higher level, i.e. further away from the substrate surface, than the at least one light source 2 in order to reduce the possibility of light from the at least one light source 2 from directly reaching the at least one photodetector 3. In an example embodiment, the at least one photodetector 3 comprises for example a photodiode, a phototransistor, a light dependent resistor (LDR) or a quantum dot enhanced graphene field effect transistor (GFET).

The apparatus 100 according to an example embodiment further comprises a first layer 4 of optical material, in an example embodiment optically absorbing or reflecting material. The first layer 4 embeds, or pots, the at least one light source 2. Furthermore, the apparatus 100 according to an example embodiment further comprises a second layer 5 of optical material, in an example embodiment optically absorbing or reflecting material. The second layer 5 comprises in an embodiment same or similar material to that of first layer 4 or in a further embodiment different material to that of first layer 4. The second layer 5 embeds, or pots, the at least one photodetector 3. The first and second layers 4 and 5 are configured to guide the light from the at least one light source 2 to the blood perfused tissue of the person using the apparatus and not to the at least on photodetector 3, since any light reaching the at least one photodetector 3 directly from the at least one light source 2 would increase measurement noise. Furthermore, the second layer 5 is configured to guide the light reflected from the skin and tissue towards the at least one photodetector 3. In an example embodiment the material of the layers 4,5 comprises optical material such as Epleguard SL1347 black coating or Epleguard SL1397 white from Peters GmbH.

The apparatus 100 according to an example embodiment further comprises a layer 6 of adhesive. The layer 6, in an example embodiment, comprises a skin safe adhesive configured to attach the apparatus 100 to the skin 7 of the user. Furthermore, in an example embodiment, the layer 6 is configured to protect the components of the apparatus 100 as they are embedded, or potted, therein. In a further example embodiment, the layer 6 of the skin safe adhesive is optically clear and is also configured to improve the optical coupling to the skin. In an example embodiment the skin safe adhesive comprises an adhesive such as Dow Corning 7-9700.

Figure 2:
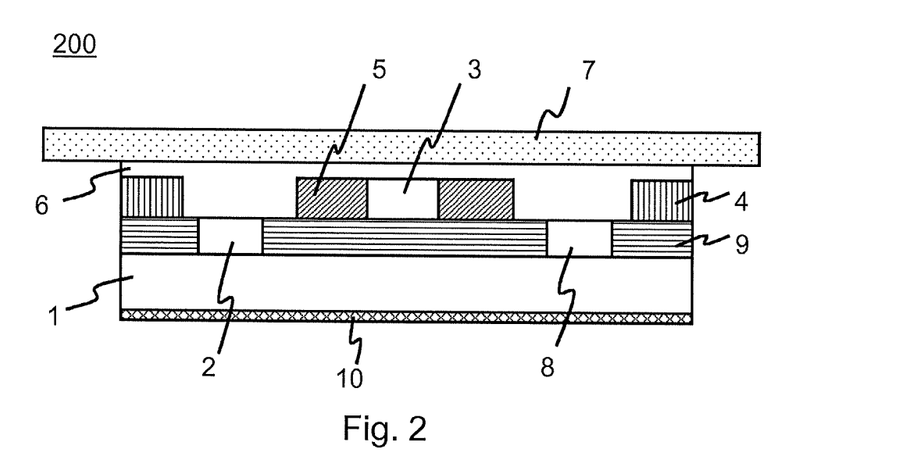
FIG. 2 shows a schematic side view of an apparatus according to a further example embodiment of the invention.

FIG. 2 shows a schematic side view of an apparatus according to a further example embodiment of the invention. FIG. 2 shows an apparatus 200 for optical biometric measurement according to an example embodiment. The apparatus 200 comprises a flexible and/or stretchable substrate 1. The substrate 1 has mounted thereon at least one light source 2, such as a light emitting diode (LED) or organic light emitting diode (OLED), configured to emit light towards and into the skin 7 and the blood perfused tissue of the person using the apparatus. In an example embodiment, the light source 2 is configured to emit green light.

The substrate 1 further has mounted thereon at least one photodetector 3. The at least one photodetector 3 is configured to detect the light reflected from the skin 7 and the blood perfused tissue of the person using the apparatus. In an example embodiment, the at least one photodetector 3 is mounted on a distance from the surface of the substrate 1 in order to reduce the possibility of light from the at least one light source 2 from directly reaching the at least one photodetector 3. In a further example embodiment, the at least one photodetector 3 is mounted on a higher level, i.e. further away from the substrate surface, than the at least one light source 2 in order to reduce the possibility of light from the at least one light source 2 from directly reaching the at least one photodetector 3. In an example embodiment, the at least one photodetector 3 comprises for example a photodiode, a phototransistor, a light dependent resistor (LDR) or a quantum dot enhanced graphene field effect transistor (GFET).

The apparatus 200 in an example embodiment further comprises at least one ambient light source 8, a reflective layer 9 and an optical element, such as a micro-lens array, 10. The ambient light source together with the reflective layer 9 is configured to guide ambient light from the micro-lens array 10 towards the skin 7 and the blood perfused tissue of the person using the apparatus, i.e. the at least one ambient light source 8, the reflective layer 9 and the micro-lens array 10 are configured to function as a waveguiding structure. In a further example embodiment, the reflective layer 9 comprises an arrangement for converting ultraviolet radiation into green light for further enhancing the PPG signal. In an example embodiment, the reflective layer 9 and the micro-lens array comprise elastomeric materials. In a still further example embodiment, the apparatus 200 comprises optical structures such as diffraction gratings in order to select specific wavelengths of light. In a further example embodiment, the at least one light source 2 is omitted, and the apparatus 200 comprises only the at least one ambient light source 8. In an example embodiment, the use of the ambient light source 8 reduces power usage of the apparatus and less, or no light from the light source 2 is required.

The apparatus 200 according to an example embodiment further comprises a first layer 4 of optical material, in an example embodiment optically absorbing or reflecting material. Furthermore, the apparatus 100 according to an example embodiment further comprises a second layer 5 of optical material, in an example embodiment optically absorbing or reflecting material. The second layer 5 comprises in an embodiment same or similar material to that of first layer 4 or in a further embodiment different material to that of first layer 4. The second layer 5 embeds, or pots, the at least one photodetector 3. The first and second layers 4 and 5 are configured to guide the light from the at least one light source 2 and the at least one ambient light source 8 to the blood perfused tissue of the person using the apparatus and not to the at least on photodetector 3, since any light reaching the at least one photodetector 3 directly from the at least one light source 2 would increase measurement noise Furthermore, the second layer 5 is configured to guide the light reflected from the skin and tissue towards the at least one photodetector 3. In an example embodiment the material of the layers 4,5 comprises optical material such as Epleguard SL1347 black coating or Epleguard SL1397 white from Peters GmbH.

The apparatus 200 according to an example embodiment further comprises a layer 6 of adhesive. The layer 6, in an example embodiment, comprises a skin safe adhesive configured to attach the apparatus 100 to the skin 7 of the user. Furthermore, in an example embodiment, the layer 6 is configured to protect the components of the apparatus 200 as they are embedded, or potted, therein. In a further example embodiment, the layer 6 of the skin safe adhesive is optically clear and is also configured to improve the optical coupling to the skin. In an example embodiment the skin safe adhesive comprises an adhesive such as Dow Corning 7-9700.

The apparatus 100,200 is configured to function as a sensor element in a photoplethysmography (PPG) measurement of heart rate, specific blood oxygen levels and further biometric measurements. The principle of PPG measurements per se are known to a skilled person. In an example embodiment, the apparatus 100,200 is formed as a thin adhesive patch, akin to plaster, that is configured to be worn on the skin of a user for a prolonged period. It is to be noted that the apparatus 100,200, in a further example embodiment, comprises elements not shown in FIGS. 1 and 2 such as interface elements. In a still further example embodiment, the apparatus 100,200 is configured to be disposable and/or recyclable after having been used. In a still further example embodiment, the apparatus 100,200 is integrated into a further device, for example a wearable device, such as into a wristwatch, smartwatch, jewelry, a piece of clothing, or an activity bracelet.

Figure 3A:
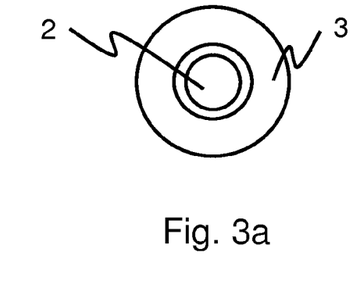
FIGS. 3a-c show schematic principle top views of an apparatus according to a further example embodiment of the invention.
Figure 3B:
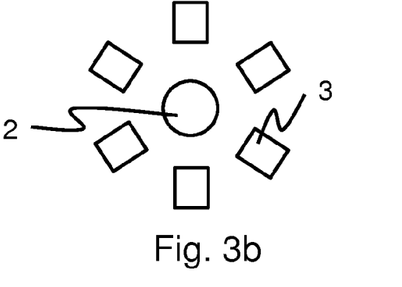
Figure 3C:
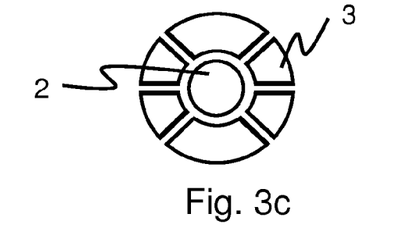

In an example embodiment, as schematically depicted in FIGS. 1 and 2, the at least one light source and/or the at least one ambient light source 8 and the at least one photodetector are positioned substantially next to each other, i.e. on the same line. FIGS. 3a to 3c show schematic principle top views of an apparatus according to a further example embodiment of the invention. FIGS. 3a-3c show arrangements of the position of the at least one light source 2 and the at least one photodetector 3 according to further example embodiments. It is to be noted that in a further example embodiment, the arrangement of the at least one ambient light source is similar to that shown in FIGS. 3a-3c. In a still further example embodiment, the apparatus 100,200 comprises several photodetectors 3 with the light sources 2,8 arranged as shown in FIGS. 1-3c.

Figure 4:
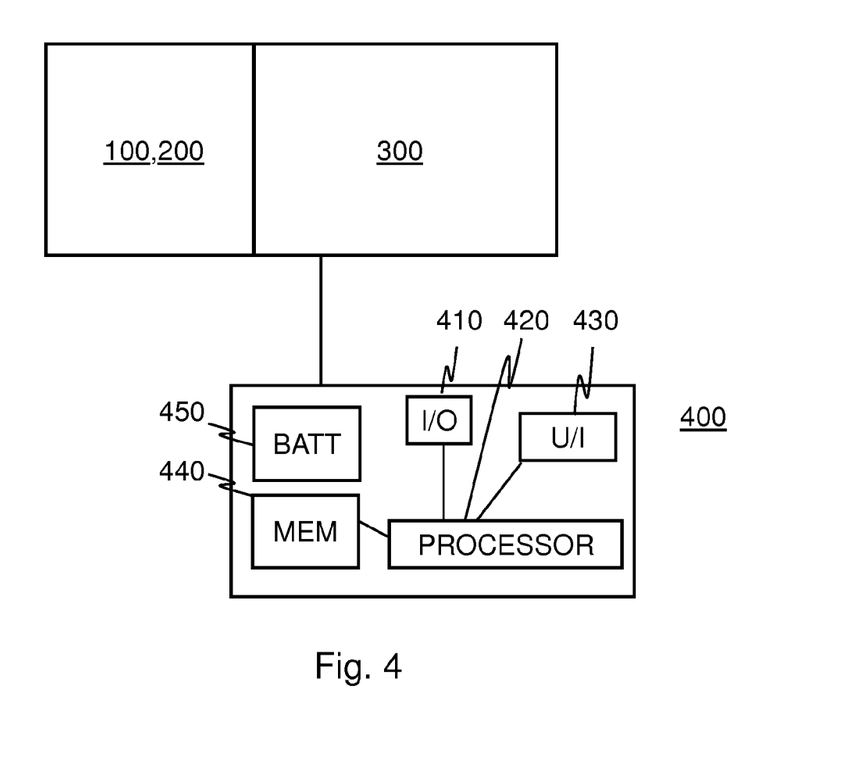
FIG. 4 shows a schematic block diagram of a system according to an example embodiment of the invention.

FIG. 4 shows a schematic block diagram of a system according to an example embodiment of the invention. The system comprises the apparatus 100, 200 as hereinbefore described according to an example embodiment of the invention. The apparatus 100, 200 is connected to a circuit element 300. In an example embodiment, the circuit element comprises a separate circuit board, or substrate, comprising electronics used with the apparatus 100, 200. In an example embodiment, the circuit element comprises a low power amplifier circuitry, for example using operational amplifiers, to which the photodetector 3 is connected. The amplifier circuit is configured to increase the sensitivity of the apparatus 100, 200 so that very small absorption changes occurring due to the pressure pulse from the heart are detected and/or specific oxygen levels ($SpO_2$) can be measured. In an example embodiment, the circuit element 300 is connected to the apparatus 100, 200 in a conventional manner, for example with wires or wirelessly with e.g. near field communication such as NFC or RFID in which case the required communication components are provided on the apparatus 100, 200 and the circuit element 300. In a still further example embodiment, the circuit element 300 is integrated with the device 100, 200, i.e. the substrate 1 of the apparatus 100, 200 has mounted thereon the amplifier circuitry.

The system further comprises a further, or power and memory, element 400. The power and memory element 400 comprises in an example embodiment a power source 450 for powering the apparatus 100,200 and the circuit element 300. In an example embodiment, the element 400 comprises a further separate power source (not shown) for powering itself. The element 400 further comprises a memory 440 and a processor 420. The processor 420 is configured to cause storing data from the apparatus 100,200 into the memory 440. The element 400 is connected to the apparatus 100,200 via the circuit element 300 in a conventional manner, e.g. in a wired or wireless manner. In a further example embodiment, the power used to power the apparatus 100,200 is also transferred wirelessly.

In a further example embodiment, the element 400 comprises a further memory (not shown) including a persistent computer program code and the processor 420 is configured to cause controlling of the operation of the apparatus 100, 200 and the element 400 itself using the computer program code. In a further example embodiment, the element 400 comprises a communication unit 410 comprising, for example, a local area network (LAN) port; a wireless local area network (WLAN) unit; Bluetooth unit; cellular data communication unit; near field communication unit or satellite data communication unit. In a further example embodiment the element 400 comprises a user interface unit 430. The processor 420 comprises, for example, any one or more of: a master control unit (MCU); a microprocessor; a digital signal processor (DSP); an application specific integrated circuit (ASIC); a field programmable gate array; and a microcontroller. In a still further example embodiment, the element 400 comprises a personal electronic device such as a wristwatch, a smart watch, an activity bracelet, a mobile phone, a smartphone, a tablet, a computer or a television, configured to co-operate with the apparatus 100, 200.

Figure 5:
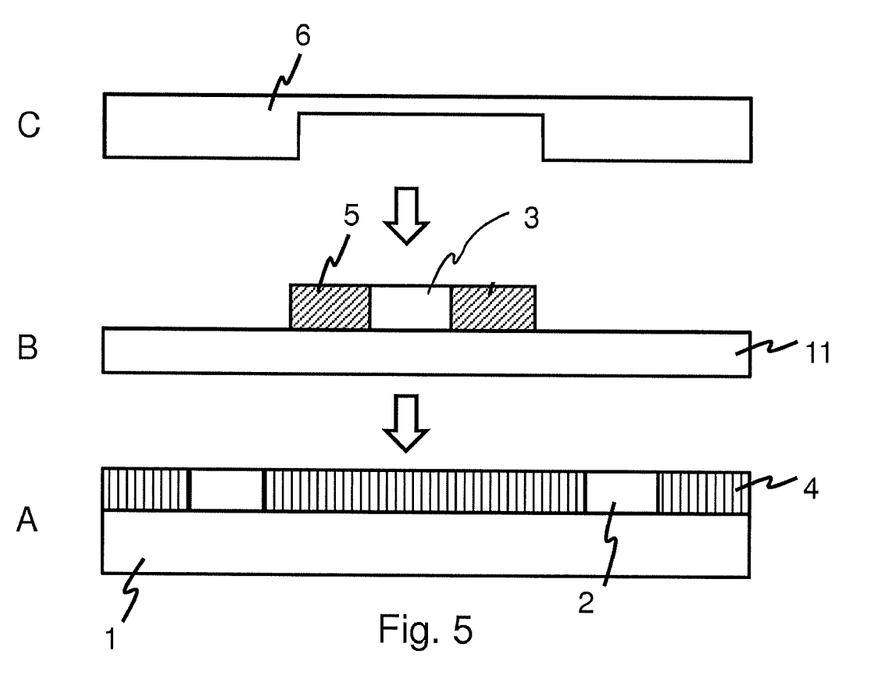
FIG. 5 shows a schematic side view of an apparatus and the assembly thereof according to an example embodiment of the invention.

FIG. 5 shows a schematic side view of an apparatus and the assembly thereof according to an example embodiment of the invention. FIG. 5 shows an apparatus 500 for optical biometric measurement according to an example embodiment. The apparatus 500 is assembled as separate layers, or laminate layers A, B, C. The apparatus 500 comprises a flexible and/or stretchable substrate 1. The substrate 1 has mounted thereon at least one light source 2, such as a light emitting diode (LED) or organic light emitting diode (OLED), configured to emit light towards and into the skin 7 and the blood perfused tissue of the person using the apparatus. In an example embodiment, the light source 2 is configured to emit green light. In a further example embodiment, the apparatus 500 further comprises in addition to or instead of the at least one light source 2, an ambient light source 8 and the related structures as described hereinbefore with reference to FIG. 2.

The apparatus 500 further comprises a further substrate 11, or detector substrate, having mounted thereon at least one photodetector 3. The at least one photodetector 3 is configured to detect the light reflected from the skin 7 and the blood perfused tissue of the person using the apparatus. The detector substrate 11 is mounted on top of the elements assembled on the substrate 1 in the laminate layer A of the process of assembling the apparatus. In an example embodiment, the at least one photodetector 3 comprises for example a photodiode, a phototransistor, a light dependent resistor (LDR) or a quantum dot enhanced graphene field effect transistor (GFET).

The apparatus 500 according to an example embodiment further comprises a first layer 4 of optical material, in an example embodiment optically absorbing or reflecting material. The first layer 4, forming a part of the laminate layer A, embeds, or pots the at least one light source 2. In an example embodiment the layer of optical material 4 is be used as adhesive to attach the second laminate layer B, i.e. the detector substrate 11. Furthermore, the apparatus 500 according to an example embodiment further comprises a second layer 5 of optical material, in an example embodiment optically absorbing or reflecting material. The second layer 5 comprises in an embodiment same or similar material to that of first layer 4 or in a further embodiment different material to that of first layer 4. The second layer 5, forming a part of the laminate layer B, embeds, or pots the at least one photodetector 3. The first and second layers 4 and 5 of apparatus 500 are configured in the same manner as hereinbefore described with reference to FIGS. 1 and 2. The apparatus 500 according to an example embodiment further comprises a layer 6 of adhesive similar to that described with reference to FIGS. 1 and 2. The layer 6, in an example embodiment, forms the laminate layer C and embeds the previous layer of the apparatus.

Although apparatuses and system according to example embodiment of the invention have been described with reference to previous FIGS. 1-5 as simply comprising the light source and detector, i.e. the sensing structures for photoplethysmography (PPG) measurement, it is envisaged that the system in an example embodiment comprises, is connected to or integrated with further sensing elements, such as temperature sensing elements, sweat analysis element, electrocardiographic sensing elements, capnographic sensing elements, position sensing elements, accelerations sensing elements and image or video based measurement elements.

Figure 6:
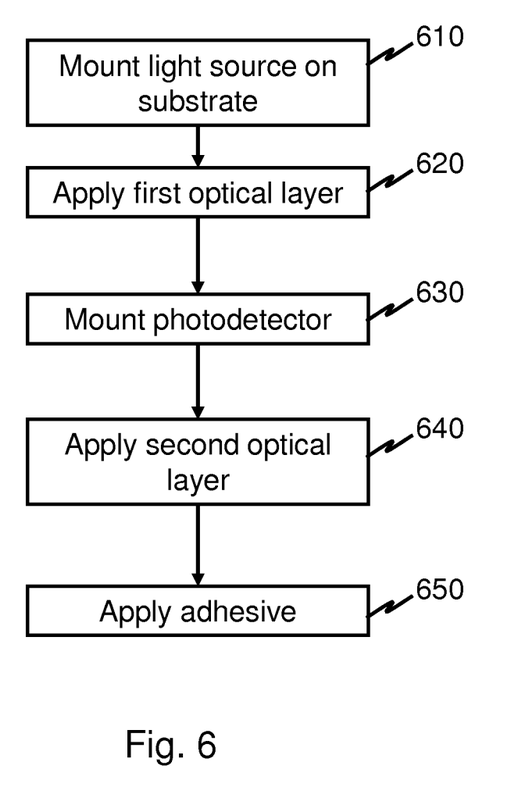
FIG. 6 shows a flow chart of a process of manufacturing an apparatus according to an example embodiment.

FIG. 6 shows a flow chart of an example process of manufacturing an apparatus according to an example embodiment. At 610 the at least one light source 2 and/or at least one ambient light source 8 is mounted on the substrate 1. In an example embodiment, the at least one light source 1. comprises surface mount components and the at least one ambient light source 8 comprises ambient light harvesting structures as hereinbefore described.

At 620 the first layer 4 of optical material is applied and encapsulates, embeds or pots the at least one light source 2 and/or the at least one ambient light source 8. In an example embodiment, the surface of the at least one light source and/or of the at least one ambient light source is treated with a de-wetting agent in order to keep the surfaces thereof clear. In an example embodiment, the reflective layer 9 configured to work as a waveguide is applied prior to the first layer 4 of optical material. In an example embodiment, the first layer 4 and/or the reflective layer 9 is applied by a method such as coating, solution processing, printing or using photopatternable materials.

At 630, the at least one photodetector is mounted on the substrate 1. In a further example embodiment, the at least one photodetector is first mounted on a further, detector, substrate 11, as shown in FIG. 5, and the detector substrate 11 is then mounted on the top of the previously installed elements at 630.

At 640, the second layer 5 of optical material is applied and encapsulates, embeds or pots the at least one photodetector. In a further example embodiment, the second layer 5 of optical material is applied prior to the detector substrate 11 being mounted. The second layer of optical material is applied in a manner similar to that of applying the first layer 4 of optical material. In an example embodiment the optical material contains oxygen and water scavenging or 'getter' materials such as zeolites or silica gel to further protect the photodetector and light source.

At 650, the skin safe adhesive is applied in such a way as to planarize the surface of the apparatus and in order for the apparatus to be configured to be attached to the skin of the user. In a further example embodiment, should the adhesive not be needed, a further embedding material with similar optical properties is used for planarizing the apparatus 100, 200, 500.

Circuits and electrodes of the apparatus 100, 200, 500 are in an example embodiment fabricated on the substrates by printing methods, such as screen, stencil and roll to roll process e.g. gravre of flexo-printing. In an example embodiment, the substrates 1,11 comprise metallized flexible substrates and are patterned by common etching processes.

Without in any way limiting the scope, interpretation, or application of the claims appearing below, a technical effect of one or more of the example embodiments disclosed herein is that low power heart rate measurements are enabled by the layers of optical material configured to guide the light. Another technical effect of one or more of the example embodiments disclosed herein is reduction of motion based data artifacts via the skin attachment. Another technical effect of one or more of the example embodiments disclosed herein is the provision of a low cost manufacturing process. A still further technical effect of one or more of the example embodiments disclosed herein is improved comfort and battery life compared to previous arrangements.

Embodiments of the present invention may be implemented in software, hardware, application logic or a combination of software, hardware and application logic. In an example embodiment, the application logic, software or an instruction set is maintained on any one of various conventional computer-readable media. In the context of this document, a "computer-readable medium" may be any media or means that can contain, store, communicate, propagate or transport the instructions for use by or in connection with an instruction execution system, apparatus, or device, with two examples of a suited apparatus being described and depicted in FIG. 4. A computer-readable medium may comprise a computer-readable storage medium that may be any media or means that can contain or store the instructions for use by or in connection with an instruction execution system, apparatus, or device, such as a computer.

If desired, the different functions discussed herein may be performed in a different order and/or concurrently with each other. Furthermore, if desired, one or more of the before-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the foregoing describes example embodiments of the invention, these descriptions should not be viewed in a limiting sense. Rather, there are several variations and modifications which may be made without departing from the scope of the present invention as defined in the appended claims.

The invention claimed is:

1. An apparatus comprising:
a first substrate layer, the first substrate layer being at least one of flexible and stretchable;
at least one light source mounted on a first side of the first substrate layer;
a first layer of optically absorbing or reflecting material embedding the at least one light source on the first side of the first substrate layer;
at least one photodetector directly mounted on and contacting a surface of the first layer of optically absorbing or reflecting material;
a second layer of optically absorbing or reflecting material embedding the at least one photodetector on the surface of the first layer of optically absorbing or reflecting material without covering the at least one light source; and
a skin-safe adhesive layer covering at least the second layer of optically absorbing or reflecting material, the skin-safe adhesive layer being provided for attaching the apparatus to skin of a user,
wherein:
the first and second layers of optically absorbing or reflecting material guide light from the at least one light source to blood-perfused tissue of the user without enabling the light to reach the at least one photodetector directly from the at least one light source;
the second layer of optically absorbing or reflecting material guides the light returning from the blood-perfused tissue towards the at least one photodetector; and
the first substrate layer, the first layer of optically absorbing or reflecting material, and the second layer of optically absorbing or reflecting material faun a laminate;
wherein, in use, the apparatus is attached to the skin of the user, the second layer of optically absorbing or reflecting material embedding the at least one photodetector facing the skin in order to perform photoplethysmographic measurements using the light from the at least one light source returning to the apparatus from the blood-perfused tissue of the user.

2. The apparatus of claim 1, wherein the at least one light source includes a light-emitting diode.

3. The apparatus of claim 1, wherein the at least one light source is configured to guide ambient light from a micro-lens array of the apparatus towards the skin of the user and the blood-perfused tissue of the user.

4. The apparatus of claim 3, wherein the micro-lens array is mounted on a second side of the first substrate layer.

5. The apparatus of claim 1, further comprising a first circuit element having a low-power amplifier circuit.

6. The apparatus of claim 5, wherein the low-power amplifier circuit is mounted on a second circuit element attached to the first circuit element.

7. A system comprising:
an apparatus comprising:
a first substrate layer, the first substrate layer being at least one of flexible and stretchable;
at least one light source mounted on a first side of the first substrate layer;
a first layer of optically absorbing or reflecting material embedding the at least one light source on the first side of the first substrate layer;
at least one photodetector directly mounted on and contacting a surface of the first layer of optically absorbing or reflecting material;
a second layer of optically absorbing or reflecting material embedding the at least one photodetector on the surface of the first layer of optically absorbing or reflecting material without covering the at least one light source; and
a skin-safe adhesive layer covering at least the second layer of optically absorbing or reflecting material, the skin-safe adhesive layer being provided for attaching the apparatus to skin of a user,
wherein:
the first and second layers of optically absorbing or reflecting material guide light from the at least one light source to blood-perfused tissue of the user without enabling the light to reach the at least one photodetector directly from the at least one light source;
the second layer of optically absorbing or reflecting material guides the light returning from the blood-perfused tissue towards the at least one photodetector; and
the first substrate layer, the first layer of optically absorbing or reflecting material, and the second layer of optically absorbing or reflecting material form a laminate;
wherein, in use, the apparatus is attached to the skin of the user, the second layer of optically absorbing or reflecting material embedding the at least one photodetector facing the skin in order to perform photoplethysmographic measurements using the light from the at least one light source returning to the apparatus from the blood-perfused tissue of the user; and
a power and non-transitory memory element connected to the apparatus.

8. The system of claim 7, wherein the power and memory element is included in a second apparatus.

9. The system of claim 8, wherein the second apparatus is selected from the group consisting of a personal electronic device, a wristwatch, a smart watch, an activity bracelet, a mobile phone, a smartphone, a tablet, a computer and a television.

10. A method of manufacturing an apparatus, wherein the apparatus comprises:
   a first substrate layer, the first substrate layer being at least one of flexible and stretchable;
   at least one light source mounted on a first side of the first substrate layer;
   a first layer of optically absorbing or reflecting material embedding the at least one light source on the first side of the first substrate layer;
   at least one photodetector directly mounted on and contacting a surface of the first layer of optically absorbing or reflecting material;
   a second layer of optically absorbing or reflecting material embedding the at least one photodetector on the surface of the first layer of optically absorbing or reflecting material without covering the at least one light source; and
   a skin-safe adhesive layer covering at least the second layer of optically absorbing or reflecting material, the skin-safe adhesive layer being provided for attaching the apparatus to skin of a user,
   wherein:
   the first and second layers of optically absorbing or reflecting material guide light from the at least one light source to blood-perfused tissue of the user without enabling the light to reach the at least one photodetector directly from the at least one light source;
   the second layer of optically absorbing or reflecting material guides the light returning from the blood-perfused tissue towards the at least one photodetector; and
   the first substrate layer, the first layer of optically absorbing or reflecting material, and the second layer of optically absorbing or reflecting material form a laminate;
   wherein, in use, the apparatus is attached to the skin of the user, the second layer of optically absorbing or reflecting material embedding the at least one photodetector facing the skin in order to perform photoplethysmographic measurements using the light from the at least one light source returning to the apparatus from the blood-perfused tissue of the user,
   the method comprising:
   mounting the at least one light source on the first side of the first substrate layer;
   applying the first layer of optically absorbing or reflecting material to embed the at least one light source on the first side of the first substrate layer;
   mounting the least one photodetector on the surface of the first layer of optically absorbing or reflecting material;
   applying the second layer of optically absorbing or reflecting material to embed the at least one photodetector on the surface of the first layer of optically absorbing or reflecting material without covering the at least one light source; and
   applying the skin-safe adhesive layer to cover at least the second layer of optically absorbing or reflecting material.

* * * * *